United States Patent
Mukhopadhyay et al.

(10) Patent No.: US 7,026,521 B1
(45) Date of Patent: Apr. 11, 2006

(54) METHANE AND METHYL CHLORIDE AS SELECTIVE REDUCING AGENT IN THE TRANSFORMATION OF HYDROCHLOROFLUOROCARBONS OR CHLOROFLUOROCARBONS TO HYDROFLUOROCARBONS

(75) Inventors: Sudip Mukhopadhyay, Buffalo, NY (US); HsuehSung Tung, Getzville, NY (US); Daniel C. Merkel, West Senaca, NY (US); Robert C. Johnson, Lancaster, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 11/091,311

(22) Filed: Mar. 28, 2005

(51) Int. Cl.
*C07C 17/00* (2006.01)

(52) U.S. Cl. .................................................. 570/157
(58) Field of Classification Search ................. 570/157
See application file for complete search history.

(56) References Cited

U.S. PATENT DOCUMENTS

| 5,414,165 | A | * | 5/1995 | Nappa et al. ................ 570/169 |
| 5,574,192 | A | * | 11/1996 | VanDerPuy et al. ......... 570/167 |
| 5,710,352 | A | * | 1/1998 | Tung ........................... 570/166 |
| 5,877,360 | A | * | 3/1999 | Moore et al. ................ 570/176 |
| 6,235,265 | B1 | * | 5/2001 | Logsdon ....................... 424/45 |

FOREIGN PATENT DOCUMENTS

| EP | 0508660 | 3/1992 |
| EP | 0347830 | 6/1999 |
| WO | WO9212113 | 7/1992 |
| WO | WO9411328 | 6/1994 |
| WO | WO9616009 | 5/1996 |
| WO | WO9617683 | 6/1996 |

* cited by examiner

*Primary Examiner*—Johann Richter
*Assistant Examiner*—Chukwuma Nwaonicha
(74) *Attorney, Agent, or Firm*—Colleen D. Szuch

(57) ABSTRACT

A gas phase reaction process for producing a hydrofluorocarbon from a hydrochlorofluorocarbon or chlorofluorocarbon reactant by contacting, in the presence of a catalyst, the hydrochlorofluorocarbon or chlorofluorocarbon reactant with a reducing agent selected from methane, methyl chloride and mixtures thereof, to produce the hydrofluorocarbon.

20 Claims, No Drawings

METHANE AND METHYL CHLORIDE AS SELECTIVE REDUCING AGENT IN THE TRANSFORMATION OF HYDROCHLOROFLUOROCARBONS OR CHLOROFLUOROCARBONS TO HYDROFLUOROCARBONS

FIELD OF THE INVENTION

This invention relates to a method for producing hydrofluorcarbons from hydrochlorofluorocarbons or chlorofluorocarbons using selective reducing agents producing a high percentage selectivity to the reduced hydrofluorocarbon product.

BACKGROUND TO THE INVENTION

Mechanical refrigeration systems, and related heat transfer devices such as heat pumps and air conditioners, using refrigerant liquids are well known in the art for industrial, commercial and domestic uses. Chlorofluorocarbons (CFCs) were developed in the 1930s as refrigerants for such systems. However, since the 1980s the effect of CFCs on the stratospheric ozone layer has become the focus of much attention. In 1987 a number of government signed the Montreal Protocol to protect the global environment setting forth a timetable for phasing out the CFC products. Subsequent amendments to this protocol accelerated the phase-out of these CFCs and also scheduled the phase-out of HCFCs. Thus, there is a requirement for a non-flammable, non-toxic alternative to replace these CFCs and HCFCs. In response to such demand industry has developed a number of hydrofluorocarbons (HFCs), which have a zero ozone depletion potential.

Hydrofluorcarbons such as difluoromethane (HFC-32), 1,1,1,2-tetrafluoroethane (HFC-134a) and 1,1,1,2,2-pentafluoroethane (HFC-125a) have essentially no ozone depletion potential (ODP) and therefore, they have been found to be acceptable refrigerants and, in some cases, as potential blowing agents in the production of plastic foams, as cleaning solvents and as propellants for aerosol sprays.

A number of processes are known for producing the desired HFC compounds. One such process involves the catalytic hydrogenation of CFC compounds in the presence of hydrogen gas. However, safety related issues associated with handling of hydrogen gas in a large scale production is always a major concern. Additionally, hydrogenation of CFCs to HFCs is often a very non-selective reaction because of the reactivity of the fluorine group with hydrogen. Such process can also involve the production of toxic chlorinated by-products. Moreover, such reactions have generally required the use of expensive catalysts, e.g., Group IB catalysts such as silver or gold catalysts, Group VIII catalysts, such as platinum or palladium catalysts, or lanthanum or lanthanide element catalysts. Example of such processes can be found for example in European Patent publications 0 347 830 and 0 508 660, PCT Patent publications WO 92 12113, WO 94 11328, WO 96 17683 A1, and WO 96 16009 A2, and U.S. Patent publication U.S. 2004167366 A1.

There is therefore a need for an improved process or synthesis method for the production of HFCs from HCFCs or CFCs that would not require the use of hydrogen gas and that is highly selective for the desired HFCs. A further need is for a improved process or synthesis method that is relatively simple to perform and can produce high conversion, up to 100% conversion, of the HCHC or CFC reactants. It would also be desirable to have such a process for conversion of HCFCs or CFCs to HFCs that can use, but does not require the use of, expensive metal catalysts, but can instead employ relatively inexpensive metal catalysts.

SUMMARY OF THE INVENTION

The process of the invention comprises a process for producing a hydrofluorocarbon from a hydrochlorofluorocarbon or chlorofluorocarbon reactant, the process comprising contacting, in the presence of a catalyst, the hydrochlorofluorocarbon or chlorofluorocarbon reactant with a reducing agent selected from the group consisting of methane, methyl chloride and mixtures thereof, in a gas phase reaction to produce the hydrofluorocarbon. The reaction may be conducted in the presence of any suitable catalyst, with or without a catalyst promoter, and is conducted in a suitable reaction vessel at a suitable time and temperature.

DETAILED DESCRIPTION OF INVENTION AND PREFERRED EMBODIMENTS

The novel process of the invention comprises a process for producing a hydrofluorocarbon from a hydrochlorofluorocarbon or chlorofluorocarbon reactant, the process comprising contacting, in the presence of a catalyst, the hydrochlorofluorocarbon or chlorofluorocarbon reactant with a reducing agent selected from the group consisting of methane, methyl chloride and mixtures thereof in a gas or vapor phase reaction to produce the hydrofluorocarbon. The process is exemplified by, but not limited by, the following reaction scheme.

$$R_FCl_n + CH_4 \text{ or } CH_3Cl \xrightarrow{catalyst} R_FH_n$$

where $R_F$ is a fluorinated alkyl group and n is a whole integer of from 1 to 3. The reaction is believed to be a free radical mechanism initiated by a heterolytic cleavage of the C—Cl bond, followed by hydrogen abstraction from $CH_4$ or $CH_3Cl$.

It has been discovered that methane and methyl chloride are selective reducing agents for producing HFCs from HCFCs or CFCs. The selectivity of reducing HCFCs or CFCs to the reduced HFCs can be as high as 95% or more at 100% HCFC or CFC conversion level.

The process of this invention is suitable for producing the reduced HFCs from any suitable HCFCs or CFCs. The HCFC or CFC reactant is preferably one of the formula $R_FCl_n$ where $R_F$ is a fluorinated alkyl group and n is a whole integer of from 1 to 3. The HCFC or CFC reactant is more preferably selected from dichlorodifluoromethane (R12), chlorotrifluoromethane (R13), chlorodifluoromethane (R22), 1,1,1,2-tetrafluoro-2,2-dichloroethane (R 114a), 1,1,1,2,2-pentafluoro-2-chloroethane (R115) and 1,1,1,2 tetrafluoro-1-chloroethane (R124).

Any suitable reducing catalyst may be employed in the process of this invention. The novel process of this invention permits the use of relatively inexpensive catalysts, such as an alkali metal catalyst. It is preferred to employ as the catalyst for the reaction either an alkali metal catalyst or nickel mesh. However, any suitable reduction catalyst may be employed, including but not limited to, Group VIII catalysts such as platinum and palladium catalysts, Group 1B catalysts such as silver and gold catalysts, as well as lanthanum and lanthanide catalyst. Any suitable alkali metal catalyst may be employed, such as a magnesium, calcium, barium and strontium catalyst. Especially preferred as a catalyst for the reaction is $Ba(NO_3)_2$ and also nickel mesh. The catalyst is preferably a supported catalyst and any suitable catalysts support, such as for example, alumina, activated carbon, and basic metal oxides, such as BaO, MgO, CaO, Cu(II) oxide and Co(III) oxide may be employed. Further examples of suitable catalyst include Pd/C and Pd/alumina, as well as Cu and Cs on a support. It is also desirable to employ any suitable catalyst promoter, such as for example, $CsNO_3$, $Cu(NO_3)_2$, $Co(NO_3)_2$, and $Pd(NO_3)_2$. Especially preferred is to employ alumina supported $Ba(NO_3)_2$ catalyst with $CsNO_3$ catalyst promoter. A preferred catalyst is nickel mesh, such as that available from Koch-Otto York, Parsippany, N.J. as Style 421, 1100 $m^2$/gm, mesh size 0.011 inch (0.028 cm).

As examples of the production of hydrofluorocarbons from hydrochlorofluorocarbons or chlorofluorocarbons in accordance with the process of this invention there may be mentioned the production of difluoromethane (R32) from dichlorodifluoromethane (R12), trifluoromethane (R23) from chlorotrifluoromethane (R13), difluoromethane (R32) from chlorodifluoromethane (R22), 1,1,1,2-tetrafluoroethane (R134a) from 1,1,1,2-tetrafluoro-2,2-dichloroethane (R 114a), 1,1,1,2,2-pentafluoroethane (R125) from 1, 1, 1,2,2-pentafluoro-2-chloroethane (R115) and 1,1,1,2-tetrafluoroethane (R134a) from 1,1,1,2 tetrafluoro-1-chloroethane (R124).

The reaction is preferably conducted in the presence of air or some oxygen to prevent the formation of carbon as product and to thereby keep the catalyst surface clean of carbon deposition.

The reaction may be conducted at any suitable temperature, generally at a temperature in the range of from about 200° C. to about 800° C., more preferably at a temperature in the range of from about 250° C. to about 725° C., and even more preferably at a temperature in the range of from about 400° C. to about 650° C.

The reaction may be conducted at any suitable pressure, generally at a pressure of from about 1 psig to about 300 psig (703.07 to 210,921 $kg/m^2$), pressure of from about 1 psig to about 100 psig (703.07 to 70,307 $kg/m^2$), and more preferably at a pressure of from about 1 psig to about 10 psig (703.07 to 7030.7 $kg/m^2$).

The reaction contact time for the reactants may be any suitable contact time, generally a time of from about 1 sec. to about 120 sec., preferably a time of from about 1 sec. to about 60 sec., and most preferably a time of from about 1 sec. to about 30 sec.

Any suitable flow rate of the reactants may be employed, such as for example a flow rate of from about 10 $cm^3$/min (sccm) to about 5000 $cm^3$/min, preferably a rate of from about 15 $cm^3$/min to about 1000 $cm^3$/min, and more preferably at a flow rate of from about 20 $cm^3$/min to about 100 $cm^3$/min.

The reaction may be conducted in any suitable reaction container or vessel, such as for example, Hastelloy®, Inconel®, Monel®, stainless steel, steel vessels, or in a Teflon lined reaction vessels.

The invention is illustrated by the following illustrative, but non-limiting examples.

Catalyst Preparation

The following are exemplifications of the preparation of catalysts employed in the process of the invention.

Catalyst—SMH1

25 gm of $BaNO_3$ was dissolved in 200 cc of DI water at 60–80° C. under constant stirring. After obtaining a clear solution, 100 gm of anhydrous γ-alumina (dried under vacuum for 60 hrs at 200° C.) was added slowly (5 gm/min) under stirring into the hot solution at 60° C. After addition of 100 gm of alumina, the mixture was stirred at 60° C. for another 45 mins. The excess water was then evaporated under vacuum at 60° C. and then the catalyst was dried at 180° C. under vacuum for 48 h. 50 cc of the freshly prepared catalyst was then charged in a Monel® reactor (Diameter—1 inch, Length—22 inch) and dried under 40 SCCM (standard cubic centimeter) of $N_2$ at 450° C. for 4 h. The temperature was then raised to 550° C. and kept for 2 h. The catalyst was then calcined at 600° C. for 1 h. Finally, the catalyst was oxidized with 20 SCCM of air at 450° C. for ½ h and with 40 SCCM of air at 450° C. for ½h.

Catalyst—SMH2

25 gm of $BaNO_3$ and 2 gm of $CsNO_3$ were dissolved in 200 cc of DI water at 60– 80° C. under constant stirring. After obtaining a clear solution, 100 gm of anhydrous γ-alumina (dried under vacuum for 60 hrs at 200° C.) was added slowly (5 gm/min) under stirring into the hot solution at 60° C. After addition of 100 gm of alumina, the mixture was stirred at 60° C. for another 45 mins. The excess water was then evaporated under vacuum at 60° C. and then the catalyst was dried at 180° C. Monel® reactor (Diameter—1 inch, Length—22 inch) and dried under 40 SCCM (standard cubic centimeter) of $N_2$ at 450° C. for 4 h. The temperature was then raised to 550° C. and kept for 2 h. The catalyst was then calcined at 600° C. for 1 h. Finally, the catalyst was oxidized with 20 SCCM of air at 450° C. for ½ h and with 40 SCCM of air at 450° C. for ½ h.

Catalyst—SMH3

25 gm of BaNO$_3$ and 2 gm of CsNO$_3$ and 1 gm of Cu(NO$_3$)$_2$ were dissolved in 200 cc of DI water at 60–80° C. under constant stirring. After obtaining a clear solution, 100 gm of anhydrous γ-alumina (dried under vacuum for 60 hrs at 200° C.) was added slowly (5 gm/min) under stirring into the hot solution at 60° C. After addition of 100 gm of alumina, the mixture was stirred at 60° C. for another 45 mins. The excess water was then evaporated under vacuum at 60° C. and then the catalyst was dried at 180° C. under vacuum for 48 h. 50 cc of the freshly prepared catalyst was then charged in a Monel® reactor (Diameter—1 inch, Length—22 inch) and dried under 40 SCCM (standard cubic centimeter) of N$_2$ at 450° C. for 4 h. The temperature was then raised to 550° C. and kept for 2 h. The catalyst was then calcined at 550° C. for 1 h. Finally, the catalyst was oxidized with 20 SCCM of air at 400° C. for ½ h and with 40 SCCM of air at 450° C. for ½ h.

Catalyst—SMH4

25 gm of BaNO$_3$ and 2 gm of CsNO$_3$ and 1 gm of Co(NO$_3$)$_2$ were dissolved in 200 cc of DI water at 60–80° C. under constant stirring. After obtaining a clear solution, 100 gm of anhydrous γ-alumina (dried under vacuum for 60 hrs at 200° C.) was added slowly (5 gm/min) under stirring into the hot solution at 60° C. After addition of 100 gm of alumina, the mixture was stirred at 60° C. for another 45 mins. The excess water was then evaporated under vacuum at 60° C. and then the catalyst was dried at 180° C. under vacuum for 48 h. 50 cc of the freshly prepared catalyst was then charged in a Monel® reactor (Diameter—1 inch, Length—22 inch) and dried under 40 SCCM (standard cubic centimeter) of N$_2$ at 400° C. for 4 h. The temperature was then raised to 550° C. and kept for 2 h. The catalyst was then calcined at 575° C. for 1 h. Finally, the catalyst was oxidized with 20 SCCM of air at 400° C. for ½ h and with 40 SCCM of air at 475° C. for ½ h.

Catalyst—SMH5

25 gm of BaNO$_3$ and 2 gm of CsNO$_3$ and 1 gm of Pd(NO$_3$)$_2$ were dissolved in 200 cc of DI water at 60–80° C. under constant stirring. After obtaining a clear solution, 100 gm of anhydrous γ-alumina (dried under vacuum for 60 hrs at 200° C.) was added slowly (5 gm/min) under stirring into the hot solution at 60° C. After addition of 100 gm of alumina, the mixture was stirred at 60° C. for another 45 mins. The excess water was then evaporated under vacuum at 60° C. and then the catalyst was dried at 180° C. under vacuum for 48 h. 50 cc of the freshly prepared catalyst was then charged in a Monel® reactor (Diameter—1 inch, Length—22 inch) and dried under 40 SCCM (standard cubic centimeter) of N$_2$ at 350° C. for 2 h. The temperature was then raised to 500° C. and kept for ½ h. The catalyst was then calcined at 575° C. for 1 h. Finally, the catalyst was oxidized with 20 SCCM of air at 300° C. for ½ h and with 40 SCCM of air at 350° C. for ½ h.

In Table 1 there are presented the results of ten catalytic reductions (Examples 1–10) of 1,1,1,2-tetrafluoro-2,2-dichloroethane (R114a) to 1,1,1,2-tetrafluoroethane (R134a) in accordance with a process of this invention.

TABLE 1

| Ex. no.[a] | Catalyst | Temp. ° C. | CH$_4$ sccm | CF$_3$CFHCl sccm | Air sccm | % Conversion of CF$_3$CFHCl[b] | % Selectivity to CF$_3$CFH$_2$[c] |
|---|---|---|---|---|---|---|---|
| 1 | SMH1 | 600 | 20 | 40 | 15 | 87 | 69 |
| 2 | SMH2 | 600 | 20 | 40 | 15 | 95 | 92 |
| 3 | SMH3 | 600 | 20 | 40 | 15 | 78 | 92 |
| 4 | SMH4 | 600 | 20 | 40 | 15 | 89 | 87 |
| 5 | SMH5 | 600 | 20 | 40 | 15 | 100 | 64 |
| 6 | SMH2 | 650 | 20 | 40 | 15 | 100 | 74 |
| 7 | SMH2 | 678 | 20 | 40 | 15 | 100 | 61 |
| 8 | SMH2 | 500 | 20 | 40 | 15 | 31 | 94 |
| 9 | SMH2 | 550 | 20 | 40 | 15 | 42 | 92 |
| 10[d] | SMH2 | 575 | 20 | 40 | 15 | 90 | 95 |

[a]Reaction conditions: pressure, 2.2–2.8 psig; catalyst, 50 cc.;
[b]Conversion is the ratio of moles of CF$_3$CFHCl reacted to the total moles taken initially multiplied by 100;
[c]% selectivity is the ratio of moles of CF$_3$CFHCl converted to CF$_3$CFH$_2$ to total moles of CF$_3$CFHCl reacted multiplied by 100;
[d]Methyl chloride is used as the reducing agent instead of using methane.

Table 1 shows results of reactions between CF$_3$CFHCl (R124) and methane (Ex. Nos. 1–b 9) or methyl chloride (Ex. No. 10). The major product was CF$_3$CFH$_2$ (R134a). CO$_2$ and CF$_3$Cl were formed as the by-products, though, in small quantities. Among several catalysts used for this reaction, SMH2 shows highest activity: 92% selectivity to R134a was obtained at a R124 conversion level of 95% (Ex. No. 2).

In the following Table 2 there is presented the results of reactions between different chlorofluorocarbons (CFCs) with methyl chloride (Ex. Nos. 11–15). 61% CF$_3$CFHCl, and 21% CF$_3$CFH$_2$ were formed when CF3CFCl2 was used as the starting material. Among other reactants, notably R12 and R22 react with methyl chloride at 550° C. in the presence of air to give R32.

TABLE 2

| Ex. No.[a] | Catalyst | T. °C. | CH₃Cl flow rate, sccm | CFC or HCFC and flow rate, Sccm | Air flow rate, sccm | % Conversion of CFC[b] | % Selectivity to products[c] |
|---|---|---|---|---|---|---|---|
| 11 | SMH2 | 600 | 20 | CF₃CFCl₂ (R114a) 40 | 20 | 100 | CF₃CFHCl, (R124) 61% CF₃CFH₂, (R134a) 21% |
| 12 | SMH2 | 600 | 20 | CF₃CF₂Cl (R115) 40 | 20 | 100 | CF₃CF₂H (R125) 83% |
| 13 | SMH2 | 600 | 20 | CF₃Cl (R13) 40 | 15 | 62 | CHF₃ (R23) 92% |
| 14 | SMH2 | 550 | 20 | CF₂Cl₂, (R12) 40 | 15 | 100 | CF₂HCl (R-22) 40% CF₂H₂ (R32) 20% |
| 15 | SMH2 | 550 | 20 | CF₂HCl, (R22) 40 | 15 | 100 | CF₂H₂ (R32), 34% |

[a]Reaction conditions: pressure, 2.2–2.8 psig; catalyst, 50 cc;
[b]conversion is the ratio of moles of CFC reacted to the total moles taken initially multiplied by 100;
[c]% selectivity is the ratio of moles of CFC converted to reduced product to total moles of CFC reacted multiplied by 100.

The reaction mechanism was studied and is believed to follow a free radical pathway. In the case of $CF_3CFHCl$, the C—Cl bond cleaves heterolytically to $CF_3CFH$ and Cl.

$$CF_3CFHCl \leftrightarrow CF_3CFH + Cl$$

followed by hydrogen abstraction from $CH_4$ $$CF_3CFH + CH_4 \leftrightarrow CF_3CFH_2 + CH_3$$

$$CH_3 + Cl \rightarrow CH_3Cl.$$

The presence of catalyst helps the initiation step (first reaction) that is in equilibrium. Methyl chloride, $CH_3Cl$, also acts similarly when used in place of methane as the hydrogen source. However, $CH_3Cl$ finally transforms to $CH_2Cl_2$ which was eventually broken into C and HCl. The presence of air is highly desirable to burn out C to $CO_2$ keeping the catalyst surface clean of carbon deposition.

While the invention has been described herein with reference to the specific embodiments thereof, it will be appreciated that changes, modification and variations can be made without departing from the spirit and scope of the inventive concept disclosed herein. Accordingly, it is intended to embrace all such changes, modification and variations that fall with the spirit and scope of the appended claims.

What is claimed is:

1. A process for producing a hydrofluorocarbon from a hydrochlorofluorocarbon or chlorofluorocarbon reactant, the process comprising contacting, in the presence of a catalyst, the hydrochlorofluorocarbon or chlorofluorocarbon reactant with a reducing agent selected from the group consisting of methane, methyl chloride and mixtures thereof, in a gas phase reaction to produce the hydrofluorocarbon.

2. The process according to claim 1 wherein the reducing agent is methane.

3. The process according to claim 1 wherein the reducing agent is methyl chloride.

4. The process according to claim 1 wherein the catalyst comprises a catalyst selected from the group consisting of an alkali metal and nickel mesh catalyst.

5. The process according to claim 2 wherein the catalyst comprises a catalyst selected from the group consisting of an alkali metal and nickel mesh catalyst.

6. The process according to claim 3 wherein the catalyst comprises a catalyst selected from the group consisting of an alkali metal and nickel mesh catalyst.

7. The process according to claim 1 wherein the hydrochlorofluorocarbon or chlorofluorocarbon reactant is a compound of the formula $R_FCl_n$ and the hydrofluorocarbon product is a compound of the formula $R_FH_n$, wherein $R_F$ is a fluorinated alkyl group and n is whole integer of from 1 to 3.

8. The process according to claim 2 wherein the hydrochlorofluorocarbon or chlorofluorocarbon reactant is a compound of the formula $R_FCl_n$ and the hydrofluorocarbon product is a compound of the formula $R_FH_n$, wherein $R_F$ is a fluorinated alkyl group and n is whole integer of from 1 to 3.

9. The process according to claim 3 wherein the hydrochlorofluorocarbon or chlorofluorocarbon reactant is a compound of the formula $R_FCl_n$ and the hydrofluorocarbon product is a compound of the formula $R_FH_n$, wherein $R_F$ is a fluorinated alkyl group and n is whole integer of from 1 to 3.

10. The process according to claim 4 wherein the hydrochlorofluorocarbon or chlorofluorocarbon reactant is a compound of the formula $R_FCl_n$ and the hydrofluorocarbon product is a compound of the formula $R_FH_n$, wherein $R_F$ is a fluorinated alkyl group and n is whole integer of from 1 to 3.

11. The process according to claim 5 wherein the hydrochlorofluorocarbon or chlorofluorocarbon reactant is a compound of the formula $R_FCl_n$ and the hydrofluorocarbon product is a compound of the formula $R_FH_n$, wherein $R_F$ is a fluorinated alkyl group and n is whole integer of from 1 to 3.

12. The process according to claim 1 wherein the hydrochlorofluorocarbon or chlorofluorocarbon reactant is selected from the group consisting of dichlorodifluoromethane, chlorotrifluoromethane, chlorodifluoromethane, 1,1,1,2-tetrafluoro-2,2-dichloroethane, 1,1,1,2,2-pentafluoro-2 chloroethane and 1,1,1,2 tetrafluoro-1-chloroethane.

13. The process according to claim 2 wherein the hydrochlorofluorocarbon or chlorofluorocarbon reactant is selected from the group consisting of dichlorodifluoromethane, chlorotrifluoromethane, chlorodifluoromethane, 1,1,1,2-tetrafluoro-2,2-dichloroethane, 1,1,1,2,2-pentafluoro-2-chloroethane and 1,1,1,2 tetrafluoro-1-chloroethane.

14. The process according to claim 3 wherein the hydrochlorofluorocarbon or chlorofluorocarbon reactant is selected from the group consisting of dichlorodifluoromethane, chlorotrifluoromethane, chlorodifluoromethane, 1,1,1,2-tetrafluoro-2,2-dichloroethane, 1,1,1,2,2-pentafluoro-2-chloroethane and 1,1,1,2 tetrafluoro-1-chloroethane.

15. The process according to claim 4 wherein the hydrochlorofluorocarbon or chlorofluorocarbon reactant is selected from the group consisting of dichlorodifluoromethane, chlorotrifluoromethane, chlorodifluoromethane, 1,1,1,2-tetrafluoro-2,2-dichloroethane, 1,1,1,2,2-pentafluoro-2-chloroethane and 1,1,1,2 tetrafluoro-1-chloroethane.

16. A process according to claim 4 wherein the catalyst is $Ba(NO_3)_2$.

17. A process according to claim 15 wherein the catalyst is $Ba(NO_3)_2$.

18. A process according to claim 16 wherein the $Ba(NO_3)_2$ is supported on alumina.

19. A process according to claim 4 wherein the catalyst is employed with a catalyst promoter.

20. A process according to claim 18 wherein the $Ba(NO_3)_2$ catalyst supported on alumina is employed with $CsNO_3$ as a catalyst promoter and the hydrochlorofluorocarbon or chlorofluorocarbon reactant is selected from the group consisting of dichlorodifluoromethane, chlorotrifluoromethane, chlorodifluoromethane, 1,1,1,2-tetrafluoro-2,2-dichloroethane, 1,1,1,2,2-pentafluoro-2-chloroethane and 1,1,1,2 tetrafluoro-1-chloroethane and the hydrofluorocarbon product is difluoromethane when the reactant is dichlorodifluoromethane, trifluoromethane when the reactant is chlorotrifluoromethane, difluoromethane when the reactant is chlorodifluoromethane, 1,1,1,2-tetrafluoroethane when the reactant is 1,1,1,2-tetrafluoro-2,2-dichloroethane, 1,1,1,2,2-pentafluoroethane when the reactant is 1,1,1,2,2-pentafluoro-2-chloroethane, and 1,1,1,2-tetrafluoroethane when the reactant is 1,1,1,2 tetrafluoro-1-chloroethane.

* * * * *